US012690658B2

(12) United States Patent
Yuvavanich et al.

(10) Patent No.: US 12,690,658 B2
(45) Date of Patent: Jul. 28, 2026

(54) CURABLE, SOLVENT REMOVABLE GEL FOR NAILS

(71) Applicant: WELLA OPERATIONS US, LLC, Calabasas, CA (US)

(72) Inventors: Sunan Yuvavanich, Thousand Oaks, CA (US); Elizabeta Pavlovic, Los Angeles, CA (US); Paul Bryson, Hidden Hills, CA (US)

(73) Assignee: WELLA OPERATIONS US, LLC, Calabasas, CA (US)

( * ) Notice: Subject to any disclaimer, the term of this patent is extended or adjusted under 35 U.S.C. 154(b) by 531 days.

(21) Appl. No.: 18/032,097

(22) PCT Filed: Oct. 13, 2021

(86) PCT No.: PCT/US2021/054664
§ 371 (c)(1),
(2) Date: Apr. 14, 2023

(87) PCT Pub. No.: WO2022/081628
PCT Pub. Date: Apr. 21, 2022

(65) Prior Publication Data
US 2023/0380569 A1 Nov. 30, 2023

Related U.S. Application Data

(60) Provisional application No. 63/091,472, filed on Oct. 14, 2020.

(51) Int. Cl.
*A61K 8/81* (2006.01)
*A45D 29/12* (2006.01)
*A61Q 3/02* (2006.01)

(52) U.S. Cl.
CPC ............ *A45D 29/12* (2013.01); *A61K 8/8152* (2013.01); *A61Q 3/02* (2013.01); *A61K 2800/43* (2013.01); *A61K 2800/81* (2013.01); *A61K 2800/95* (2013.01)

(58) Field of Classification Search
None
See application file for complete search history.

(56) References Cited

U.S. PATENT DOCUMENTS

| | | | |
|---|---|---|---|
| 7,282,551 B2 | 10/2007 | Hoff et al. | |
| 10,619,098 B2 | 4/2020 | Reddy et al. | |
| 2013/0263875 A1* | 10/2013 | Burgess | A61K 8/72 132/73 |
| 2016/0223269 A1 | 8/2016 | Hartmann et al. | |
| 2017/0119650 A1* | 5/2017 | Xu | A61K 8/466 |
| 2018/0092827 A1 | 4/2018 | Sheran et al. | |
| 2020/0093730 A1 | 3/2020 | Herrlein et al. | |

OTHER PUBLICATIONS

International Search Report in connection with PCCT/US2021/054664 issued on Jan. 12, 2022.
International Written Opinion in connection with PCCT/US2021/054664 issued on Jan. 12, 2022.

* cited by examiner

*Primary Examiner* — Nicole P Babson
(74) *Attorney, Agent, or Firm* — Dennemeyer & Associates LLC

(57) ABSTRACT

Photopolymerizable topcoat and color coat gel compositions suitable for forming a photopolymerized nail coating are described. Both gel compositions include a mixture of one or more pre-formed polymers, a (meth)acrylic monomer, a multi-(meth)acrylate crosslinker, a UV photoinitiator and an antioxidant. The color coat gel composition includes pigments, a smectite clay and silica.

5 Claims, No Drawings

CURABLE, SOLVENT REMOVABLE GEL FOR NAILS

CROSS-REFERENCE TO RELATED APPLICATION

This application is a U.S. National Stage Filing under 35 U.S.C. 371 from International Application No. PCT/US2021/054664, filed on Oct. 13, 2021 and published as WO 2022/081628 on Apr. 21, 2022, which application claims priority to U.S. Provisional Application No. 63/091,472, filed Oct. 14, 2020, all of which applications are incorporated herein by reference in their entirety.

BACKGROUND

Commercial gel nail coatings typically include a base coat, a color coat and a topcoat. Recent developments in the technology combine pre-existing film forming polymers such as cellulose acetate butyrate with photopolymerizable gels based upon (meth)acrylate technology. The gels include crosslinkers that contribute hardness, resistance to dissolution, resistance to scratching and long wear yet in combination with film formers contribute flexibility. Nail salons are the typical commercial establishments handling this work because it entails careful application and curing by UV radiation.

These coatings most often become hard and rigid upon curing. While these beneficial attributes contribute to long-lasting nail coatings that resist scratching and damage, these attributes are also problematic. A nail polymer coat should be removable. Once applied and cured, the coating is difficult to remove and typically requires abrasion, sanding, chipping and striking to obtain adequate removal.

To solve this problem, nail polymer coat manufacturers have lowered the degree of crosslinking, employed additional components to soften the photopolymerized or cured coating and incorporated solvent-soluble film formers to enable solvent removal. The patent literature describes attempts to provide a cured nail coat that is both tough, flexible, scratch and abrasion resistant yet can be easily removed by soaking the cured or photopolymerized coating in organic solvent. The literature describes nail polymer coatings composed of (meth)acrylate monomers, di and tri (meth)acrylate crosslinkers and compatible preformed polymeric film formers that deliver tough, flexible cured nail coatings that can be removed by soaking with organic solvent.

These cured compositions include interpenetrating networks of mutually incompatible polymeric materials so that substantially homogeneous coatings are not produced. Instead, these coatings have a continuous phase of polymeric material in which is dispersed a separate discontinuous phase of a second material. Typically, such interpenetrating networks are formulated with cellulose derivatives which deliver hardness to the non-polymerized domains and are susceptible to dissolution by organic solvents. However, interpenetrating networks formulated with cellulose derivatives tend to develop cured coatings that are too hard, are inflexible and can be susceptible to cracking and breakage. Therefore, there is a need to develop nail coatings that are both readily removable while demonstrating strength, toughness and avoidance of cracking and breaking.

SUMMARY

The present invention is directed to topcoat and color coat gels that are capable of establishing single phase interpenetrating networks of solvent soluble polymer interspersed with solvent insoluble in situ produced polymer yet are flexible and durable. The cured topcoat and color coat gels are capable of being removed with coating removal solvents without the need for abrasion and sanding. The present invention is also directed to a method of application the topcoat and color coat gels and to the cured color/topcoat on a nail.

Compositional aspects of the topcoat and color coat gels comprise at least one pre-formed polymer, an aminoalkyl (meth)acrylate monomer and a multi-(meth)acrylate crosslinker. The gel topcoat composition comprises at least a polyester as the pre-formed polymer. The polyester may have a degree of crosslinking that enables the polyester to exhibit at least some solubility in ordinary cosmetic organic solvents. The gel color coat composition comprises at least a polyester, an epoxy-tosylamide resin and a styrene-acrylates copolymer as pre-formed polymers. At least one of the polyester, resin and copolymer may have a degree of crosslinking that enables the at least one to exhibit at least some solubility in ordinary cosmetic organic solvents. Both of the gel topcoat and color coat preferably comprise at least a dimethyl or diethylaminoalkyl methacrylate as the (meth)acrylate monomer and a trimethylolpropane tri(meth)acrylate or tetramethylol methane tetra(meth)acrylate as the multi-acrylate crosslinker. More preferably, the multi-acrylate crosslinker for both is trimethylolpropane triacrylate. The compositional aspects of the topcoat and color coat also comprise a UV photoinitiator and an anti-oxidant/free radical scavenger to prevent extraneous, free radical oxidation of the compositional components. The typical UV photoinitiator and antioxidants incorporated into the compositions include benzophenone and butylated hydroxytoluene. The gel color coat composition also comprises an aluminum phyllosilicate clay, mineral particles and color pigments. Both of the gel topcoat and the color coat are preferably substantially to essentially free of organic solvent, aqueous medium and non-reactive organic liquids not typically considered solvents.

The topcoat and color coat gels are single phase, substantially to essentially homogeneous mixtures of the components of the compositions. They are stable and do not separate into individual components.

The cured topcoat and color coat are produced by exposure of the uncured gel compositions to UV radiation, also known as actinic radiation for a period of time sufficient to photopolymerize the monomeric (meth)acrylate and the multi-acrylate crosslinker. The pre-formed polymer(s) are miscible within the photopolymerized (meth)acrylate network. The combination is believed to form interlaced pre-formed polymers within a continuous network domain of polymerized methacrylates.

Application of the topcoat and color coat gels may be accomplished by brush, spray, drip or similar application technique. The color coat gel is applied first. Because the color coat is a gel, it at least substantially maintains its form in an uncured state so that the topcoat gel may be applied directly over the uncured color coat gel. Nevertheless, the color coat gel in an uncured state may optionally be exposed to UV radiation for a period of time to at least partially polymerize the monomer and crosslinker. Following the optional partial cure of the color coat gel, the top coat gel is applied. The applied layers of color coat and topcoat gels may then be exposed to UV radiation to fully cure both gels.

If designs are to be made, the first portion of color coat gel may be applied as an outline or other appropriate configuration of the design. Following the cure of the first portion, subsequent portions of appropriate color coat gels may be sequentially applied and cured to for the desired design. Application can be accomplished by artistic means such as would be applied by watercolor or oil base paint and easel.

A typical cured gel coat according to the invention comprises a clear topcoat applied over the color coat. According to the invention, aspects of the topcoat and color coat involve the same UV curable compositional aspects. The topcoat is clear while the color coat contains added color components as well as additional pre-formed polymers, an aluminum phyllosilicate clay and mineral particles.

DETAILED DESCRIPTION

The present invention is directed to topcoat and color coat gel compositions that are sequentially applied to a substrate such as a nail and may be photopolymerized to produce a solid, abrasive resistant, flexible coating of polymerized (meth)acrylate components and one or more pre-formed polymers. The resultant cured nail coating is a substantially interspersed network of the crosslinked (meth)acrylate component interspersed with the one or more pre-formed polymers. The interspersed network provides polymer miscibility rather than polymer separation.

Definitions

Unless defined otherwise, all technical and scientific terms used herein have the same meaning as commonly understood by a person of ordinary skill in the art.

As used in the specification and the appended claims, the singular forms "a," "an" and "the" include plural referents unless the context clearly dictates otherwise.

The term "may" in the context of this application means "is permitted to" or "is able to" and is a synonym for the term "can." The term "may" as used herein does not mean possibility or chance.

The (meth)acrylate moiety as a monomer or as an oligomeric or polymeric terminating group is an acrylate or methacrylate ester compound wherein the esterifying alcohol is preferably an aliphatic monoalcohol or a tertiary amino alcohol. The aliphatic group preferably is an alkylenyl group of two to 10 carbons or is a branched or cyclic alkyl group of three to 10 carbons. The parenthesis surrounding the prefix "meth" means that the term (meth) acrylate encompasses methacrylic acid and acrylic acid compounds. Without a parenthesis, the term methacrylate means only the methacrylate esters, and does not include acrylic esters. The suffix "ate" means that the term (meth) acrylate is an ester formed by combination of a monoalcohol or tertiary amino alcohol with methacrylic acid or acrylic acid. Preferred (meth)acrylate monomer is dimethyl or diethylamino alkyl (meth)acrylate and the preferred (meth) acrylate is methacrylate.

The term "tertiary" associated with amine groups means the amine nitrogen is bound to three carbon groups. Examples of tertiary amines are trimethyl amine, dimethylamino ethanol and methyl, di-(hydroxyethyl) amine.

The crosslinker multi-(meth)acrylate is a short chain alkyl moiety having multiple (meth)acrylate moieties as three or four short chains bound to the alkyl moiety. The short chain alkyl moiety may be a C1 to C10 alkyl group, preferably a methyl, ethyl or propyl group to which is bound three or four hydroxymethyl groups. Preferred examples include pentaerythritol and trimethylolpropane with four and three hydroxyl groups respectively. The hydroxyl groups may be esterified with (meth)acrylic acid to form the multi-(meth) acrylate crosslinker.

The (meth)acrylate monomers are liquids and act as reactive solvents for the solid components of the topcoat and color coat compositions.

The molecular weight of a polymer or oligomer used according to the invention may be measured by a weight average molecular weight. The distribution of molecules of different molecular weights of a polymer or oligomer used according to the invention is determined by its polydispersity index. Molecular weight is expressed as Daltons (Da), kiloDaltons (kDa) and million Daltons (MDa). The acronym "wmw" stands for weight average molecular weight. Polydispersity is a unit-less number and indicates the breadth of the Gaussian curve plotted as the molecular weight of individual molecules (X axis) against the number of molecules at each molecular weight (Y-axis).

The terms "photopolymerizable" and "photopolymerized" are understood to mean respectively a polymerizable mixture of ingredients and a polymerized material. Synonyms for photopolymerizable and photopolymerized are curable and cured or polymerizable and polymerized.

The term gel is understood to mean a semi-solid composition that has flow properties under pressure such as through brush, spray or spatula application but exhibits substantially little to no flow in a steady, quiescent state. Gels in general exhibit some crosslinking among their components caused by one or more crosslinking or intermolecular interactions such as covalent crosslinking, hydrogen bond crosslinking, and/or lipophilic entanglement. In the present context, the pre-formed polymer(s) are believed to establish molecular entanglements that at least in part largely contribute to this gel state. Additionally, hydrogen bonding among the epoxy-tosylamide resin, the ester groups and the amine groups may contribute to this gel state. However, it is believed that no considerable degree of covalent crosslinking of the components of the gel compositions occurs before curing.

The term "about" is understood to mean ±10 percent of the recited number, numbers or range of numbers.

The term "about 0 wt %" is understood to mean that no substance, compound or material to which zero (0) refers is present, up to a negligible but detectable amount is present, assuming that the detectability can be determined on a parts per million basis.

The term "non-solvent" is understood to mean no organic liquid solvent such as ethyl acetate, methyl ethyl ketone, acetone, mono alcohols such as methanol, ethanol, propanol or butanol, or any other organic solvent having an STP boiling point of 100° C. or lower is present and in which the pre-formed polymers will dissolve.

Where features or aspects of the invention are described in terms of Markush groups, those skilled in the art will recognize that the invention is also thereby described in terms of any individual member or subgroup of members of the Markush group. For example, if X is described as selected from the group consisting of methyl, ethyl or propyl, claims for X being methyl and claims for X being methyl and ethyl are fully described. Moreover, where features or aspects of the invention are described in terms of Markush groups, those skilled in the art will recognize that the invention is also thereby described in terms of any combination of individual members or subgroups of members of Markush groups. Thus, for example, if X is described as selected from the group consisting of bromine, chlorine, and iodine, and Y is described as selected from the group consisting of methyl, ethyl, and propyl, claims for X being bromine and Y being methyl are fully described.

If a value of a variable that is necessarily an integer, e.g., the number of carbon atoms in an alkyl group or the number of substituents on a ring, is described as a range, e.g., 0-4, what is meant is that the value can be any integer between 0 and 4 inclusive, i.e., 0, 1, 2, 3, or 4.

The Topcoat and Color Coat Gel

The topcoat and color coat gels comprise a composition of at least one tertiary aminoalkyl (meth)acrylate monomer, a multi-(meth)acrylate crosslinker and at least one pre-formed polymer. Additional components of these gel compositions may include a photoinitiator such as benzophenone and/or an oxidation, free-radical inhibitor such as butylated hydroxytoluene. The color coat gel may include additional components such as colorant particles, mineral micropar-ticles, aluminum phyllosilicate clay particles such as smec-tite clays. The color coat gel may further include additional pre-formed polymers including an epoxy resin and a sty-rene-(meth)acrylates copolymer. The topcoat and color coat gels are a non-solvent, substantially homogeneous mixture of these components.

The pre-formed polymer of topcoat and color coat gel compositions may be at least a polyester. The polyester may be an alkyl polyester formed of a linear or branched satu-rated alkyl dicarboxylic acid, a linear or branched saturated alkyl diol and an aromatic or alkyl tricarboxylic acid cross linker or an anhydride of an aromatic or alkyl tricarboxylic acid cross linker.

The diacid may contain from 3 to 10 carbons in the alkyl chain with two carboxylic acid groups preferably but not necessarily at the termini of the chain. The total number of carbons of the diacid therefore may be 5 to 12 carbons including the two carboxylic acid groups.

The diol may contain from 2 to 10 carbons in the alkyl chain with the hydroxyl groups preferably but not necessar-ily at the termini of the chain.

The tricarboxylic acid crosslinker may be a phenyl tri-carboxylic acid such as trimellitic anhydride or trimesic acid or an alkyl tricarboxylic acid of from 3 to 10 carbons in the alkyl chain such as a C3-C10 $\alpha,\beta,\omega$ tricarboxylic acid, examples of which may be propane-1,2,3-tricarboxylic acid and butane-1, 2,4-tricarboxylic acid.

The polyester may be most preferably constructed of a preferred dicarboxylic acid, diol and crosslinker comprising adipic acid, neopentyl glycol and trimellitic anhydride. The crosslinking may be negligible, slight, low or moderate so that the polyester has at least some solubility in ordinary cosmetic organic solvents. The crosslinking may not be of a degree that prevents at least some solubility of the polyester in ordinary cosmetic organic solvents.

As mentioned above, the color coat gel composition may be a combination of a styrene-acrylates copolymer and an epoxy-sulfonamide resin and the crosslinked polyester described above. The styrene-acrylates copolymer is olefinic copolymer formed from styrene and a combination of acrylic acid and one or more alkyl acrylates with the acrylic acid being present, if any, at a low to very low molar percentage.

The epoxy-sulfonamide resin is a pre-formed polymer of a bis-(alkyl or arylglycidyl ether) alkane such as 2,2-bis-(4-phenylglycidyl ether) propane with sulfonamide terminal and/or pendant groups such as produced from p-tosylsulfo-namide and is a commercially available resin available for nail coatings and cosmetics. Depending on the manufacturer, this resin may, but not necessarily, contain at least some residual epoxy groups. If residual epoxy groups are present, this resin may be capable of chain extending and crosslinking in situ to form longer polymer chain networks. The chain extension and crosslinking may occur with nucleophilic reactants such as carboxyl, amine, hydroxyl and sulfonamide groups. Consequently, the resin may, but not necessarily, produce at least minor crosslinking and chain extension with the other pre-formed polymer compo-nents present. The extent of such in situ chain extension and cross linking in and among the pre-formed polymer com-ponents depends upon the extent of such residual groups. The presence of such combinable residual groups among any and/or all of the pre-formed polymers may be notice-able, negligible or non-existent.

All of these pre-formed polymer(s) are commercially available, film forming polymers used in the cosmetic indus-try and are soluble in typical organic cosmetic solvents and insoluble in water. Their weight average molecular weights vary according to the manufacturing source. Typical weight average molecular weights of the pre-formed polymers may be in the range of about 1 kDa to about 1 MDa, preferably about 5 kDa to about 500 kDa, more preferably about 5 kDa to about 200 kDa. These pre-formed polymers may exhibit a degree of crosslinking ranging from negligible to moderate so that at least one of the pre-formed polymers may exhibit at least some solubility in ordinary cosmetic organic sol-vents.

The topcoat and color coat gels include at least one (meth)acrylate monomer and at least one multi-(meth)acry-late crosslinker that together may be photopolymerized in situ, to form a (meth)acrylate polymer network. The (meth)acrylate monomer may be a tertiary aminoalkyl (meth)acrylate monomer such as but not limited to di-C1-C3-alkylamino-C1-C3-alkyl (meth)acrylate. A preferred embodiment of this monomer is a dimethyl- or diethyl-amino-C1-C3-alkyl (meth)acrylate. A more preferred embodiment is a dimethyl- or diethyl-amino ethyl (meth) acrylate. An especially, more preferred embodiment is a dimethylamino ethyl methacrylate. The multi-(meth)acry-late crosslinker may be a C1-C4-alkylol-C1-C4-alkylenyl tri or tetra (meth)acrylate, preferably a methylol-C1-C4-alkyle-nyl tri or tetra (meth)acrylate. Embodiments include trim-ethylolpropane triacrylate and tetramethylol methane tet-raacrylate. A preferred embodiment is trimethylolpropane triacrylate.

For the topcoat gel composition, the weight ratio between the pre-formed polymer component and the photopolymer-izable component may range from about 0.5:1 to about 1.1:1, preferably about 0.7:1, more preferably about 0.8/0.9: 1. For the color coat gel composition, the weight ratio between the preformed polymer component and the photo-polymerizable component may range from about 0.7:1 to about 1.1:1, preferably about 1:1 to 1.1:1. The pre-formed polymer component of the topcoat and color coat gel com-positions includes the polyester. Additionally, the pre-formed polymer component of the color coat gel composi-tion includes the styrene-(meth)acrylates copolymer and epoxy-sulfonamide resin. The photopolymerizable compo-nent includes the tertiary aminoalkyl (meth)acrylate mono-mer and the multi-(meth)acrylates crosslinker.

These weight ratios for pre-formed polymer component to photopolymerizable component according to the present invention are atypical of standard nail coatings. Standard nail coatings with pre-formed polymer components typically exhibit weight ratios of pre-formed polymer to polymerizable component on the order of 0.1-0.4:1. In other words a much lower amount of pre-formed polymer relative to the polymerizable component.

It is well known that a crosslinking polymerization process involves a fluid stage at the outset of polymerization and a solidified stage as polymerization and crosslinking proceed. The ultimate result of a crosslinked polymer is achievement of a solidified stage in which a molecular component having a network structure, infinite molecular weight and size is produced. In other words, the monomer and crosslinker in this construction have been joined together as a single molecular network. This network is impervious to most exogenous agents and holds the monomeric units of the polymer in a substantially inflexible, non-translatable form. The topcoat and color coat gel compositions of the present invention include pre-formed polymers which act as hurdles toward formation of a network composed of a single polymeric molecule of infinite size. The pre-formed polymers are intermixed with the polymerizing monomer and crosslinker so that the pre-formed polymers inhibit the translational motion of the unpolymerized monomers and oligomers as polymerization proceeds. This lack of translational motion inhibits full and complete polymerization of the monomer and crosslinker into a single network. The typical result of the pre-formed polymer hurdles inhibiting this process is the production of a large number of polymer molecules of varying lengths interspersed among the pre-formed polymer(s). Although it is not a limitation of the invention, it is believed that this interspersion coupled with the large weight ratio of pre-formed polymer component to polymerizable component is at least in part responsible for the strong yet flexible cured coating that may be readily removed with typical organic solvents without the need for significant abrasion and/or chipping and scraping.

The monomer concentrations in the topcoat and color coat gel compositions on a weight percentage basis relative to the total weight of the composition range from about 35 to about 45 weight percent (wt %), preferably about 36 to about 38 weight percent, for the topcoat and about 28 to about 32 wt %, preferably about 29 to about 31 wt %, for the color coat (including the pigment weight). The multi-(meth)acrylate crosslinker concentrations in the topcoat and color coat gel compositions range from about 14 to about 17 wt %, preferably about 15 to about 16 wt %, for the top coat and about 9 to about 12 wt %, preferably about 10 to about 11 wt %, for the color coat (including the pigment weight). The pre-formed polymer concentration in the topcoat gel composition ranges from 40 to 44 wt %, preferably about 41 to about 42 wt %. The pre-formed polymer concentration in the color coat gel composition ranges from about 40 to about 44 wt % in total, preferably about 41 to about 43 wt % in total.

The pre-formed polymer components in the color coat composition individually range from about 15 to about 17 wt % for the polyester and/or the styrene-(meth)acrylates copolymer and/or about 9 to about 11 wt % for the epoxysulfonamide resin.

Any suitable photoinitiator or combination may be combined with the other components of the topcoat and color coat gels to enable photopolymerization. Benzophenone and phosphine oxide photoinitators can be employed with benzophenone preferred. A typical concentration of the photoinitiator may range from about 4 to about 6 wt % relative to the total weight of the composition.

Inclusion of one or more polymerization regulators and anti-oxidation agents may also be desirable. These include hydroquinones and ascorbic acid derivatives as well as butylated hydroxytoluene. These regulators and agents may range in concentration from 0.3 wt % to about 0.6 wt %.

Inorganic pigments and dyes such as ferric oxide; FD&C red 4, 6, 7, 17, 21, 22, 27, 28 or 33; FD&C yellow 5 or 6; D&C violet 2, 3 or 4; titanium oxide; D&C orange 4, 5 or 10; FD&C green 3, 5 or 6, and similar colorants may be employed. Suitable concentrations of total pigments and dyes range from 8 wt % to 12 wt %.

An additional component of the color coat comprises an aluminum phyllosilicate clay such as a smectite clay, examples of which being bentonite, hectorite, montmorillonite or sepiolite clay. The smectite clays are intercalated with quaternary ammonium salts (hereinafter alkonium salts). The resulting intercalated alkonium aluminum phyllosilicates enable the clays to form stable suspensions in organic solvent. The exchange of alkonium salts for the naturally intercalated inorganic salts present between the lamellar microcrystalline sheets of smectite clays shifts the nature of the smectite clays from hydrophilic/ion exchange to lipophilic and enables stable suspensions in non-polar organic solvents as well as in aqueous/organic solutions. Such smectite clays intercalated with alkonium salts according to the invention enable sustained suspension of the coating pigments and management of viscosity so that pigments do not settle before curing and the composition does not flow or run, e.g., is in a gel state. The preferred smectite clays are stearalkonium bentonite or stearalkonium sepiolite. Although it is not a limitation of the invention, it is believed that use of sepiolite clay may lessen and/or negate the tendency of the color coat gel composition to produce N-nitrosamines such as NDMA, NDMA and NMBA. The concentration of the smectite clay in the color coat gel composition relative to the total weight of the composition ranges from about 1 wt % to about 2 wt %.

Another viscosity modifier and particulate suspension agent is a microparticulate mineral oxide such as silica and/or titanium oxide. The particulate size ranges from 1 to 100 microns and the concentration relative to the total weight of the color coat composition ranges from 0.4 to 0.6 wt %.

Surfactants, plasticizers and emulsifiers such as phthalates, camphor, castor oil, citrate esters, glyceryl diesters, glycolates and tartrates may be included as appropriate. Typical concentrations of about 0.2 wt % to about 1.0 wt % may be employed.

The topcoat composition may have a viscosity of at least about 750 to 800 cP and a density of about 1 to 1.1 g per ml. The color coat composition may have a viscosity of about 2400 to about 2500 cP and a density of about 1 to 1.1 g per ml.

The topcoat gel of the invention may be applied as a clear topcoat to a bare nail or to a nail pre-coated with a base coat and/or with the color coat composition described above.

Application of the topcoat and color coat gels of the invention is accomplished by ordinary salon techniques. Use of fine brushes, fine spray pencils and sponge wipers are typical applicators useful for applying the topcoat and color coat gels to nails and coated nails. Exposure to UV radiation produced with a UV light source will initiate polymerization. Dual UV wavelengths of the 405 and 365-385 nm ranges can be employed to photopolymerize the topcoat and color coat gels. The times for exposure may range from 1 to 2 minutes.

Multiple applications of the topcoat and color coat gels may also be employed especially if multicolor partial layers and/or designs are to be produced. Fine tip brush work similar to an artist painting with brush and easel can be employed for this purpose. Following each partial application, the applied coating can be exposed to UV radiation. However, the topcoat and color coat gels used for such designs can be prepared to present a higher thixotropic property than is present in a single coating for the entire nail. In this manner, a single UV radiation can be applied following completion of the design and the design can be altered.

EXAMPLES

Amounts in Weight Percentages (wt %)

| Component | Topcoat | Color Coat no pigment | Color Coat pigment |
|---|---|---|---|
| Adipic acid/neopentyl glycol/trimellitic anhydride copolymer | 41-42 | 17-18 | 16-17 |
| Dimethylaminoethyl methacrylate | 37-38 | 33-34 | 30-31 |
| Trimethylolpropane triacrylate | 15-16 | 11-12 | 10-11 |
| Tosylamide/epoxy resin in 25% butyl acetate | — | 11-12 | 10-11 |
| Styrene-acrylates copolymer | — | 17-18 | 10-11 |
| Red pigment/wax/titanium triisostearate | — | — | 3-4 |
| Red 33/wax/titanium triisostearate | — | — | 6-7 |
| Benzophenone | 5 | 5 | 4-5 |
| Butylated hydroxytoluene | 0.4-0.5 | 0.4-0.5 | 0.4-0.5 |
| Silica | — | 0.6 | 0.5-0.6 |
| Stearalkonium bentonite | — | 1-2 | 0.4-0.6 |
| Total | 100.0 | 100.0 | 100.0 |

The preparation of the gel composition utilizes a two-step process in which the color coat gel is coated onto the nail, optionally at least partially cured and then the topcoat gel is applied onto the color coat gel. The two layer coating is irradiated with a UV cure light for approximately 60 seconds for each coat. The cured coating has a high gloss, is abrasion resistant and flexible. The uncured color coat and topcoat gels contain essentially no non-reactive solvent. The cured coating may be removed with acetone, methyl ethyl ketone, ethanol, or mixtures thereof in approximately 5 minutes or less.

Miscellaneous Statements

The inventions, examples and results described and claimed herein have may attributes and embodiments include, but not limited to, those set forth or described or referenced in this application.

All patents, publications, scientific articles, web sites and other documents and ministerial references or mentioned herein are indicative of the levels of skill of those skilled in the art to which the invention pertains, and each such referenced document and material is hereby incorporated by reference to the same extent as if it had been incorporated verbatim and set forth in its entirety herein. The right is reserved to physically incorporate into this specification any and all materials and information from any such patent, publication, scientific article, web site, electronically available information, text book or other referenced material or document.

The written description of this patent application includes all claims. All claims including all original claims are hereby incorporated by reference in their entirety into the written description portion of the specification and the right is reserved to physically incorporate into the written description or any other portion of the application any and all such claims. Thus, for example, under no circumstances may the patent be interpreted as allegedly not providing a written description for a claim on the assertion that the precise wording of the claim is not set forth in haec verba in written description portion of the patent.

While the invention has been described in conjunction with the detailed description thereof, the foregoing description is intended to illustrate and not limit the scope of the invention, which is defined by the scope of the appended claims. Thus, from the foregoing, it will be appreciated that, although specific non-limiting embodiments of the invention have been described herein for the purpose of illustration, various modifications may be made without deviating from the scope of the invention. Each embodiment and each aspect so defined may be combined with any other embodiment or with any other aspect unless clearly indicated to the contrary. Other aspects, advantages, and modifications are within the scope of the following claims and the present invention is not limited except as by the appended claims.

What is claimed is:

1. A topcoat composition consisting of: a single phase mixture of a preformed crosslinked polyester of C5-C12 alkyl-dicarboxylic acid, a C2-C10 diol and an aromatic or alkyl tricarboxylic acid or anhydride thereof, a (meth)acrylate monomer of di-C1-C3 alkylamino C1-C3 alkyl methacrylate, a multi-(meth)acrylate crosslinker of trimethylolpropane triacrylate or tetramethylol methane tetraacrylate, a UV photoinitiator and an antioxidant, wherein;

the preformed crosslinked polyester concentration is about 40 wt. % to about 44 wt. %, the (meth)acrylate monomer concentration is about 35 wt. % to about 45 wt. %, the cross-linker concentration is about 14 wt. % to about 17 wt. %, the weight ratio of the weight amount of the preformed crosslinked polyester to the weight amount of the combination of monomer and crosslinker is in a range of about 0.5:1 to about 1.1:1, the (meth)acrylate monomer is a solvent for and solubilizes the preformed crosslinked polyester, the preformed crosslinked polyester is soluble in organic solvent, and the topcoat composition is a homogeneous, clear, stable, single phase mixture, does not separate into individual components, is essentially free of organic solvent and aqueous medium, and optionally includes one or more of a free radical scavenger, a polymerization regulator, a plasticizer, a surfactant and an emulsifier.

2. The topcoat composition according to claim 1 having a viscosity of at least 750 cP and/or a density of about 1 g per ml.

3. The topcoat composition according to claim 1 wherein the polyester has a wt. avg. MW of from about 5 kDa to about 500 kDa and the wt. % ratio of preformed crosslinked polyester to monomer is about 0.89:1 to about 1.26:1.

4. The topcoat composition according to claim 1 wherein the polyester is a crosslinked polyester copolymer of adipic acid, neopentyl glycol and trimellitic anhydride, and/or the (meth)acrylate monomer is dimethylaminoethyl methacrylate, and/or the crosslinker is trimethylolpropane triacrylate, wherein the weight ratio of the copolymer to the combination of monomer and crosslinker is in a range of 0.6:1 to about 1.1:1.

5. The topcoat composition according to claim 1 wherein the photoinitiator is benzophenone and/or the antioxidant is butylated hydroxytoluene.

\* \* \* \* \*